United States Patent [19]

Streich et al.

[11] Patent Number: 5,175,355
[45] Date of Patent: Dec. 29, 1992

[54] PROCESS FOR RECOVERY OF PURIFIED TEREPHTHALIC ACID

[75] Inventors: Debra J. Streich, Naperville; Diane J. Graziano, Clarendon Hills; Sandra K. Schiller, Naperville; Roger J. Grimm, Glen Ellyn, all of Ill.

[73] Assignee: Amoco Corporation, Chicago, Ill.

[21] Appl. No.: 810,725

[22] Filed: Dec. 18, 1991

Related U.S. Application Data

[63] Continuation-in-part of Ser. No. 685,218, Apr. 12, 1991, abandoned.

[51] Int. Cl.⁵ ............................................. C07C 51/43
[52] U.S. Cl. .................................. 562/485; 562/486; 562/494
[58] Field of Search .................. 562/485, 486, 494

[56] References Cited

U.S. PATENT DOCUMENTS 3,624,145  11/1971  Brian ................................. 562/485
4,340,752   7/1982  List et al. ........................... 562/485

Primary Examiner—Jose G. Dees
Assistant Examiner—Vera C. Clarke
Attorney, Agent, or Firm—Gunar J. Blumberg; Wallace L. Oliver; Frank J. Sroka

[57] ABSTRACT

A process is disclosed for preparation of purified terephthalic acid containing 200 ppmw or less of p-toluic acid. A filter cake of purified terephthalic acid is prepared by filtering, under a differential pressure of about or greater than 0.5 psi over the system pressure and a temperature within the range of from about 100° C. to about 205° C., an aqueous slurry of purified terephthalic acid containing a solution of p-toluic acid. The aqueous solution of p-toluic acid remaining in the filter cake of purified terephthalic acid is displaced from the filter cake by water under a pressure gradient over the system pressure at a temperature within the range of from about 100° C. to about 205° C. Pressure flash evaporation of water remaining in the filter cake occurs upon release of the system pressure to lower pressure with consequent lower temperature. The crystalline terephthalic acid product containing 200 ppmw or less p-toluic acid can be dried under atmospheric pressure. Purified terephthalic acid is useful for the manufacture of polyesters from which clothing and related goods are made.

12 Claims, No Drawings

PROCESS FOR RECOVERY OF PURIFIED TEREPHTHALIC ACID

This is a continuation-in-part of application Ser. No. 685,218 filed Apr. 12, 1991, now abandoned.

FIELD OF THE INVENTION

The field of the invention relates to an improved process for recovery of purified terephthalic acid (hereinafter PTA) from an aqueous slurry containing a solution of p-toluic acid. Purified terephthalic acid is prepared wherein the concentration of p-toluic acid is less than 200 parts per million by weight (ppmw). In the oxidation of paraxylene to terephthalic acid, 4-carboxybenzaldehyde is produced as an intermediate. In the purification of the terephthalic acid in the presence of water, the 4-carboxybenzaldehyde is hydrogenated to a more water soluble derivative, p-toluic acid. The purified terephthalic acid containing residual p-toluic acid is washed with water to remove residual soluble p-toluic acid. The wash water containing the p-toluic acid is recycled or discarded to waste treatment facilities. A process of flooded water washing under pressure of the purified terephthalic acid operates to reduce amount of wash water, to decrease content of residual impurities in purified terephthalic acid, and/or, to decrease the load on downstream waste treatment capacity. This invention substitutes the pressure centrifugation, reslurry, atmospheric pressure flashing and atmospheric pressure separation steps utilized in prior art processes to recover purified terephthalic acid from an aqueous slurry by a single unit operation, i.e., pressure filtration, with consequent lower equipment costs.

BACKGROUND OF THE INVENTION

Usually, terephthalic acid is produced by a liquid phase oxidation of p-xylene and/or p-toluic acid. Terephthalic acid is of great commercial importance and is widely used for the production of various different polymers, such as fiber-forming polyesters. A process for preparing polyesters of terephthalic acid, particularly polyethylene terephthalate, comprises a direct condensation of terephthalic acid with the respective polyalcohol. For example, terephthalic acid is reacted with ethylene glycol to from bis($\beta$-hydroxyethyl) terephthalate which is then polymerized in a second stage. This direct condensation process is simpler than other known methods such as transesterification of dimethyl terephthalate with the appropriate glycol. However, the direct esterification requires the use of medium or highly purified terephthalic acid. In order to be suitable for the production of polyester fibers, terephthalic acid must be substantially free of any contaminants which lower the melting point of the polyester and/or cause coloration of the polyester. In fact, some impurities which are contained in crude terephthalic acid are color-forming precursors.

All these impurities have not yet been identified. However, 4-carboxybenzaldehyde which is an intermediate oxidation product and which in the following is abbreviated as 4-CBA, generally is found in crude terephthalic acid. It is known that the degree to which coloration in the polyester is induced is less if the 4-CBA content of the terephthalic acid is low. While pure 4-CBA itself does not necessarily promote coloring during polymerization, this impurity is a convenient tracer for evaluating the degree to which terephthalic acid has been refined. A process which can reduce the 4-CBA content of terephthalic acid reduces also the content of color-forming precursors.

Commercial crude terephthalic acid contains on a weight basis from 800 to 7,000 parts per million (ppm) 4-carboxybenzaldehyde and 200 to 1,500 ppm p-toluic acid as the main impurities. Crude terephthalic acid also contains lesser amounts, 20-200 ppm range, of yellow color aromatic compounds having the structures of benzil, fluorenone or anthraquinone which are characteristically yellow compounds as impurities resulting from coupling side reactions occurring during the oxidation of p-xylene.

U.S. Pat. No. 3,584,039 issued to Delbert H. Meyer teaches a feasible, commercially useful method for purification of such commercially available crude terephthalic acid products by treating liquid phase solutions thereof in water at temperatures of 200°-374° C. with hydrogen in the presence of a solid hydrogenation catalyst (e.g. metallic palladium on carbon support) and crystallizing terephthalic acid from catalyst-free liquid phase solutions at temperatures in the range of 50° C. to 150° C. The catalytic hydrogen treatment converts 4-carboxybenzaldehyde to p-toluic acid and decolorizes the terephthalic acid.

British Pat. No. 1,152,575 is directed to the development of the Meyer Patent method for its commercial application providing improved modes of conduct for the entire process from the step of dissolving crude terephthalic acid through the step of crystallizing terephthalic acid from the hydrogen treated aqueous solution. With respect to said crystallization, said British patent teaches the use of solvent evaporation to effect the cooling necessary to precipitate crystalline terephthalic acid but cautions that conduct of such evaporative cooling should avoid shock cooling of the solution as would occur by instantaneous flash evaporation of solvent because such shock cooling coprecipitates dissolved impurities which contaminate terephthalic acid product. To prevent the contaminating effect of such shock cooling, the British patent teaches that the evaporative cooling should be controlled by evaporation against equilibrium back pressure, for example, by throttling of steam vapor exhaust at the equilibrium pressure. This is in effect a controlled rate evaporative cooling.

Crystallization by controlled rate evaporative cooling is, according to the above British patent, applied to continuous crystallization conducted in three series connected stages under the conditions described to effect in 3.4 hours a 150° C. temperature drop from 277° C. initial solution temperature to the third stage temperature of 109° C. This mode of conducting said crystallization provided an average cooling rate of 1.48° F. per minute that was not only inordinately slow but, when applied to aqueous solutions of terephthalic acid of 2,400 ppm p-toluic acid content, also provided a terephthalic acid product containing 1,200 ppm p-toluic acid. Such product would not be acceptable for direct reaction with ethylene glycol for polyester fiber manufacture.

U.S. Pat. No. 3,452,088 repeats the caution against shock cooling and teaches a further improvement for the continuous controlled rate evaporative cooling technique as applied to crystallizing terephthalic acid from aqueous solutions also containing dissolved p-toluic acid. The improvement consists of limiting the final crystallization temperature and/or crystalline product separation temperature to the temperature range of 121° to 149° C. to prevent p-toluic acid contamination of crystallizing terephthalic acid. By using such final crystallization and/or product separation temperatures of 121° to 149° C. terephthalic acid could be and was commercially obtained with 150 ppm and less p-toluic acid from feed solutions containing 500 to 6,000 ppm p-toluic acid at a somewhat faster cooling rate of 3°-4° F. per minute. But such faster controlled rate evaporation process does not provide a useful basis for devising still faster continuous flash evaporative crystallization to overcome the p-toluic acid contamination problem mentioned in both the British and U.S. patents.

Crystallization by flash evaporation of solvent has, in general, been long known and used to take advantage of the substantially instantaneous decrease in both temperature and pressure and attendant substantially instantaneous evaporation of solvent as the hot solution of solute is introduced into the crystallization vessel operated at a lower temperature and pressure. Advantageously, the rapidly vaporized portion of the liquid solvent flashed to the vapor phase permits rapid removal of solvent vapor. Both crystallization and crystal growth occur rapidly with the cooling and concentrating caused by flashing the solution to the lower temperature. Growth of crystals is substantially entirely the result of the lower temperature and is independent of residence time. Crystal size in a crystallization vessel where solvent is flash evaporated can, as is well known, be enhanced by circulation of slurry of crystals throughout the lower portion of the crystallization vessel. For example, one means for accomplishing such circulation in a stirred crystallization zone is to withdraw a portion of the slurry from near its upper level and introduce, e.g., by pumping, the withdrawn slurry up through the bottom of the stirred slurry.

However, use of flash solvent evaporation induced crystallization of terephthalic acid (TA) from aqueous solution also containing dissolved p-toluic acid in amounts of 500 to 6,000 ppm based on TA can, without proper conduct thereof, bring into play the p-toluic acid contamination phenomenon alluded to in the British patent and more generally described in the later U.S. patent. Such contamination phenomenon is somewhat anomalous because, in spite of the fact that there is retained more than enough solvent water to prevent saturation or supersaturation with respect to p-toluic acid, p-toluic acid nevertheless comes out of solution. Said later U.S. patent suggests that the contamination phenomenon is in some way dependent on the rate of crystallization and the final temperature of crystallization and product separation and not solely on p-toluic acid concentration in the solution.

From plots of TA saturation and supersaturation (TA concentrations vs. temperature) and the guidance provided by teachings in the aforementioned related British and United States patents, one might devise a continuous TA crystallization process having a number of crystallization stages in series with each stage operated at a temperature lower than the preceding stage and, for smooth operation approximating batchwise crystallization, having a temperature profile substantially following the TA saturation plot. Such a devised continuous crystallization process would have at least about 40 rate-dependent crystallization stages. However, because of the number of stages and their time consuming operation, such a continuous crystallization would not be economically attractive or feasible for commercial application.

It is therefore an object of this invention to provide a method for displacing p-toluic acid from a slurry of purified terephthalic acid in an aqueous medium wherein the aqueous medium containing the p-toluic acid is displaced from the slurry of purified terephthalic acid by a positive displacement method using pressure filtration of the purified terephthalic acid in a method of flooded water washing, also termed plug flow washing, of the filter cake, at high temperature and pressure, followed by release of the pressure with consequent lower temperature and, ultimately, to a condition of atmospheric pressure. The concentration of p-toluic acid retained in the purified terephthalic acid is equal to or less than 200 ppmw.

It is an object of this invention to provide a method for displacing p-toluic acid from a slurry of purified terephthalic acid in an aqueous medium wherein the p-toluic acid is displaced from the slurry of purified terephthalic acid by a positive displacement method using filtration of the purified terephthalic acid slurry under high temperature and pressure wherein the concentration of p-toluic acid retained in the filter cake is equal to or less than 200 ppmw and pressure is reduced to atmospheric pressure.

It is further an object of this invention to provide an improved process for preparation of purified terephthalic acid containing 200 ppmw, or less, of p-toluic acid and the purified terephthalic acid is at atmospheric pressure, and is thereby in a state to be processed by a dryer at atmospheric pressure.

SUMMARY OF THE INVENTION

A process of producing purified terephthalic acid (TA) having 200 ppm or less p-toluic acid content by weight (i.e., fiber-grade quality TA) has been discovered which is applicable to aqueous slurries of TA having 500–6,000 ppm by weight of p-toluic acid in solution. The aqueous slurry containing the crystallized TA and an aqueous solution of dissolved p-toluic acid is filtered. The filter cake is subject to a process for positive displacement of the aqueous solution of the p-toluic acid at a temperature of at from about 38° C. to about 205° C. and at a pressure differential of from about 0.5 psi to about 65 psi over the system pressure. The aqueous solution containing the soluble p-toluic acid is displaced by water under pressure from the filter cake of crystalline TA by pressure filtration at high temperature. The solution of p-toluic acid remaining in the filter cake is displaced by water under pressure. Pressure flash evaporation of water remaining in the filter cake occurs upon release of the system pressure and a consequent lower temperature to atmospheric pressure. The crystalline product of terephthalic acid containing 200 ppm or less p-toluic acid is thereupon subjected to drying equipment under atmospheric pressure to obtain desired product.

DETAILS OF THE INVENTION

In an embodiment of this invention, an alkyl aromatic, such as paraxylene and/or p-toluic acid, oxidized in an acetic acid medium with molecular oxygen in the presence of a catalyst system containing bromine and one or more heavy metals such as cobalt, manganese and the like. Although this method is well-known in the art and is commercially used, the oxidation reaction results in impurities which can be removed or rendered colorless to obtain a fiber-grade terephthalic acid. The principal use of captive and non-captive terephthalic acid is and has been for the manufacture of high molecular weight polyesters for fiber and film manufacture.

From U.S. Pat. No. 3,584,039, it is known that fiber grade terephthalic acid can be prepared by purifying crude terephthalic acid by means of a reduction procedure. The process is essentially comprised of treating an aqueous solution of crude terephthalic acid with hydrogen in the presence of a supported or unsupported Group VIII metal catalyst wherein the metal and the support are insoluble in the solution under the working conditions. By this process, intermediate oxidation products, such as 4-carboxybenzaldehyde (4-CBA) and other coloring impurities in terephthalic acid are reduced and form removable products. Purified terephthalic acid is then recovered by crystallization and dried.

Although the above procedure has various advantages, problems remain in that the contamination of purified terephthalic acid with p-toluic acid is a cooling rate dependent phenomenon rather than a temperature dependent phenomenon. Flash temperature reduction occasioned by release of pressure operates to precipitate p-toluic acid from the solution of purified terephthalic acid upon crystalline purified terephthalic acid. However, solubility of p-toluic acid remains high in the aqueous medium at a temperature of from about 38° C. to about 205° C.

Surprisingly, it has been found that positive displacement of the aqueous solution of p-toluic acid from a filter cake of crystalline purified terephthalic acid effectively displaces the p-toluic acid from contact with the purified terephthalic acid by displacing the aqueous solution of p-toluic acid with water at high temperature and pressure. The pressure is then released to an ambient atmospheric condition. The concentration of p-toluic acid retained in the crystalline purified terephthalic acid thereupon has been found to be equal to or less than 200 ppmw.

In the process of the instant invention, the purified terephthalic acid crystals from a crystallizer in the aqueous medium are filtered at a temperature of at least about 38° C., preferably from about 100° C. to about 205° C. at a pressure of at least about 0.5 psig, preferably within the range of from about 40 psig to about 110 psig, to develop a filter cake.

The aqueous slurry containing crystals of purified terephthalic acid is introduced into a filter cell, or a series of filter cells, physically situated to permit a filter cake to develop of a sufficiency and distribution to cover the area of the filter cell to hinder or prevent the development of channeling of wash water. Suitably, a filter cake of at least about 0.5 inch in depth to about 8 inches, preferably at least about 1 inch in depth, more preferably about 2 to about 4 inches in depth is developed over the area of the filter cell. The aqueous mother liquor can be recoverd and treated to recover p-toluic acid and/or sent to waste treatment facilities.

Upon obtaining a suitable or preferred height of filter cake, about 0.5 inch to 8 inches, the cake leaves the filtration zone and enters a washing zone where the cake is washed with a water stream at a pressure gradient to allow a reservoir buildup of water over the filter cake to a suitable depth, preferably to a minimum depth of about 0.25 inch. A pressure gradient of at least 0.5 psi over the system pressure, preferably from 5 psi to about 65 psi over the system pressure, is thereupon applied to the water stream to displace the aqueous solution of p-toluic acid from the filter cake in a positive displacement method. The water-washed cake of purified terephthalic acid is thereupon subject to release of system pressure to a pressure within the range of from atmospheric pressure to about 90 psig with attendant reduction of system temperature to a temperature equal to or less than about 166° C. The water-washed purified terephthalic acid is thereupon dried under atmospheric pressure.

A minimum cake depth of purified terephthalic acid of at least 0.5 inch is suitable to obtain a filter cake of sufficient compactness to furnish a wash vehicle, i.e. the filter cake, from which a solution containing a solute can be removed efficiently by displacement washing. If cake depth is less than about 0.5 inch, retention of solution containing a solute by the filter cake is increased significantly despite application of wash water at increased pressure. Because of the loss of efficiency in displacement washing of the filter cake by water to remove a solution containing a dissolved solute, a minimum filter cake depth of at least 0.5 inch, of purified terephthalic acid is preferred.

A minimum liquid height above the cake surface is required to ensure that displacement washing occurs. This height must be sufficient to ensure that the cake surface is completely covered with liquid. If the cake surface is not covered with water, bypassing of the wash liquor can occur without complete displacement of mother liquor from the interior of the cake. Because of irregularities in the cake surface, a minimum liquid height of about 0.25 inch is preferred over the cake surface.

It has been found that positive displacement of an aqueous solution of p-toluic acid using water as the displacing medium in a filtration cycle at high temperature and pressure permits an efficient exchange of the p-toluic acid solution for a medium comprising water and recovery of the purified terephthalic acid from the aqueous component of the slurry which contains soluble p-toluic acid. The positive displacement of the solution of p-toluic acid from the filter cake of purified terephthalic acid at elevated temperature and pressure diminishes the co-crystallization of p-toluic acid with the crystallization of purified terephthalic acid at a pressure equal to or less than 235 psig and a temperature equal to or less than about 205° C. upon release of the system pressure and decrease of system temperature.

Because of the insolubility of p-toluic acid in water at temperatures below 38° C. and pressures below 10 psig, typical filtration techniques are unsuitable to remove p-toluic acid from the filter cake. Although the solubility problem can be partially overcome by filtration at elevated temperature and pressure, filtration and water washing are typically less successful in removing p-toluic acid from crystalline purified terephthalic acid wherein a vacuum is used or wherein pressure filtration is used without use of a method of plug flow washing or flooded water washing. Such vacuum or pressure filtration procedures can result in the channeling of the cake and the water wash does not penetrate the cake.

In the process of the instant invention it has been found that unexpected efficiencies of removal of p-toluic acid can be obtained by pressure displacement washing of the filter cake comprising purified terephthalic acid. P-Toluic acid in purified terephthalic acid can be reduced to 200 ppmw, or less.

From an engineering standpoint, the added stages of the pressure filter allow the pressure to be decreased to atmospheric pressure, thus alleviating problems caused by solids discharge to a dryer operating at atmospheric pressure. In an embodiment of the process of the instant invention, a rotary valve can be used to decrease system pressure to atmospheric pressure.

Utilization of added stages of pressure displacement washing can decrease the amount of water required to reduce the level of p-toluic acid retained in the cake of purified terephthalic, as has been demonstrated by the reduction of water required by utilization of added stages of positive displacement washing to reduce the amount of water required to reduce the level of acetic acid retained from an aqueous solution of acetic acid.

It is convenient therefore that a suitable number of stages of positive displacement washing be used to minimize total water used in displacement washing to reduce need for downstream waste treatment facilities. Accordingly, for the process of the instant invention for positive displacement of p-toluic acid from mother liquor retained in filter cake of purified terephthalic acid to obtain a level equal to or less than about 200 ppm in the cake by filtration, a multi-stage displacement washing of the purified terephthalic acid can be used.

It is of course understood that a multi-stage displacement washing procedure can be replaced by a single stage displacement washing procedure wherein the quantity of wash water is sufficient to obtain a level equal to or less than about 200 ppm of p-toluic acid retained in the purified terephthalic acid. Additionally, a procedure of counter-current washing can be useful if reduction of the amount of wash water is determined to be advantageous.

In the process of the instant invention, a p-toluic acid slurry containing crystals of purified terephthalic acid is introduced into one or more of a series of filter cells physically situated to permit a filter cake of requisite thickness to develop by passage of a stream of the slurry of purified terephthalic acid. Upon obtaining a minimum height of filter cake, about 0.5 to about 8 inches, the cake leaves the filtration zone and enters a washing zone where the cake is washed with a water stream. Pressure is applied thereupon to the water stream to displace the p-toluic acid in the mother liquor retained in the filter cake by positive pressure. Upon displacement of the water reservoir through the filter cake, the filter cake is discharged from the filter by suitable means and the cycle is repeated. The ratio of wash area to cake formation area is within the range of from about 1:20 to about 20:1 to reduce the level of p-toluic acid in the filter cake. The system pressure is thereupon released and the washed filter cake is discharged from the filter.

Equipment for performing the requisite cycle can comprise a series of filter cells maintained in a suitable position to permit a water flood to develop over the filter cells. Suitable equipment can comprise a rotary drum filter with multiple filter cells, and fitted with means for discharging washed filter cake from the filter cells. Control means are required for introducing a stream comprising purified terephthalic acid in a p-toluic acid solution to develop a filter cake to transport the filter cake from the filtration zone to a washing zone where the filter cake is washed by a stream of water, wherein the water is under pressure to cause positive displacement of the p-toluic acid in the mother liquor retained in the purified terephthalic acid. The filter cake can be washed for as many times as required to develop a minimum concentration of p-toluic acid in the filter cake before discharging the washed filter cake from the rotary drum filter.

A suitable rotary drum filter which can be adapted to the requirements of the instant invented process is a BHS-FEST (TM) pressure filter, BHS-WERK, Sonthofen, D-8972, Sonthofen, West Germany, although other filters which can accomplish the required cycle of operation can be used, such as a belt filter from Pannevis, b.v., Utrecht, Holland, or other suppliers.

In the operation of the BHS-FEST TM filter, a rotary drum contains a series of filter cells located on the periphery of the rotating drum. As the drum rotates, the filter cells receive an aqueous slurry of purified terephthalic acid and soluble p-toluic acid and a filter cake builds to a requisite depth. Upon rotation of the drum, the filter cake leaves the filtration zone and enters the washing zone to build a reservoir of water over the filter cake to a required depth. The applied pressure to the water reservoir forces the water through the filter cake to displace the p-toluic acid retained in the water upon the crystals of purified terephthalic acid. Upon further rotation of the drum, the wash cycle can be repeated at least one more time if necessary, after which the system pressure is released with attendant temperature decrease to an ambient condition. The filter cake is thereupon charged from the drum by application of an inert gas under pressure.

A similar sequence of operations occurs with use of a belt filter.

EXAMPLE I

The following example illustrates the process of the instant invention using a BHS-FEST (TM) filter.

Slurry, containing 45% crystallized PTA solids and mother liquor, is fed to a BHS-FEST (TM) rotary pressure filter at 60 psig pressure, and 149° C. temperature. A BHS-FEST (TM) filter is employed to separate the solids from the mother liquor, wash the solids, remove excess cake moisture, and discharge the solids at atmospheric pressure. The filter housing is divided into five chambers to perform five different operations—filtration/cake formation, displacement wash, cake drying, cake discharge, and filter cloth rinse. The filter drum, operating at speeds ranging from 0.5 to 2.0 rpm, is divided into twenty filter cells. The total filter cloth area available on the drum is about 1.3 ft$^2$. Slurry capacity is about 360, 720 and 1440 lbs/hr flow rate when the filter operator is at 0.5, 1.0 and 2.0 rpm, respectively.

As the filter operates continuously, all of the operations—filtration/cake formation, displacement wash, cake drying/discharge, and filter cloth rinse-occur simultaneously. The operation is described by illustrating the history of one filter cell.

The filter cell rotates into the filtration/cake formation chamber. The feed slurry, containing about 45% PTA solids and about 1,000 ppmw p-toluic acid, is pumped continuously into the chamber at about 60 psig pressure. As the filter cell rotates through the chamber, the solids build up on the filter cloth to a 1 inch cake thickness. The mother liquor passes through the filter cloth into an internal pipe in the filter. The pressure of the mother liquor in this internal pipe ranges from about 30 to about 50 psig. The mother liquor is sent to p-toluic acid recovery facilities and/or waste treatment.

The filter cell, now containing a formed cake, leaves the filtration/cake formation chamber and rotates into the displacement chamber. Clean water is pumped continuously into the chamber at a pressure of about 60 psig and about 149° C. This useful temperature range for the clean water is about 82° C. to about 149° C. This water, via the effectiveness of displacement washing, effectively removes p-toluic acid from the filter cake. Wash water which has passed through the cake is now at a pressure of about 30 to about 50 psig. This water is collected separately from the mother liquor and used elsewhere in the PTA process.

The washed cake in the filter cell leaves the displacement wash chamber and enters the cake drying chamber. Compressed inert gas, at a pressure of about 60 psig, is introduced continuously into the drying chamber to remove excess water from the filter cake.

The filter cell then rotates from the drying chamber into the cake discharge chamber. In contrast to the other described chambers, this chamber operates at ambient pressure. Because of the pressure drop from the cake drying chamber to the cake discharge chamber, some additional moisture is flashed from the cake. The cake is then discharged from the filter at a flow rate of about 190, 380, or 760 lb/hr for a filter speed of about 0.5, 1.0 or 2.0 rpm, respectively. The final cake has a p-toluic acid concentration of 200 ppmw or less on a dry-cake basis.

After discharging the cake, the filter cell is rinsed with water in the filter cloth rinse chamber to remove any traces of undischarged cake. The filter cell then enters the filtration/cake formation chamber and repeats the process.

Data for relevant experiments are indicated in Table I. The wash ratio indicates the amount of clean water used to displacement wash the cake from p-toluic acid, measured as a ratio of cake flow rate. The blow ratio indicates the amount of compressed inert gas used to dry the cake prior to discharge, measured as a ratio of cake flow rate.

TABLE I

| Example Number | Filter Speed rpm | Wash Ratio lb water/lb PTA | Wash Temp deg C. | Blow Ratio SCFH/lb PTA | Delta Form Pressure psi | Cake Wetness wt % | P-Toluic Acid on Cake, ppm |
|---|---|---|---|---|---|---|---|
| 2 | 0.531 | 0.773 | 88 | 0.855 | 19 | 14.7 | 112 |
| 3 | 0.531 | 2.783 | 127 | 0.855 | 18 | 12.4 | 106 |
| 4 | 1.03 | 1.241 | 126 | 0.441 | 9 | 12.2 | 103 |
| 5 | 1.03 | 0.381 | 88 | 0.441 | 17 | 14.5 | 113 |
| 6 | 1.97 | 1.151 | 90 | 0.231 | 11 | 17.5 | 111 |
| 7 | 1.97 | 0.436 | 133 | 0.231 | 14 | 11.7 | 113 |

EXAMPLE 8

The following example illustrates the process of the instant invention using a beltfilter.

Slurry, containing 48% crystallized PTA solids and mother liquor, is fed to a pressurized beltfilter at a 780 lbs/hr flow rate, 90 psig pressure, and 166° C. temperature. The beltfilter performs operations in three zones—separation of solids from the mother liquor, displacement washing, and drying.

The slurry is fed to the first section of the belt, where the solids and mother liquor are separated. The solids form a continuous 3 inch thick cake on the belt. The mother liquor filtrate passes through the filter cloth and is pumped either to p-toluic acid recovery facilities and/or waste treatment.

The continuous cake is then conveyed into the displacement washing zone. This zone also operates at 90 psig and 166° C. In this zone, clean water is fed above the cake at a flow rate which maintains a liquid level above the cake.

After the displacement washing zone, the continuous cake enters the cake drying zone. The excess water is allowed to drain from the cake and inert gas is introduced to further remove the moisture. This zone also operates at 90 psig and 166° C.

The dried cake, now containing only 200 ppmw or less p-toluic acid on a dry basis, is discharged from the belt into a pressure reducing device(s), such as a sealed screw conveyor or a series of rotary valves. The PTA cake, now at atmospheric pressure, is then transferred to an atmospheric dryer.

We claim:

1. A process for the preparation of purified terephthalic acid containing p-toluic acid present in a concentration equal to or less than 200 parts per million by weight which process comprises:
   (a) introducing into a filter cell or a series of filter cells in a filtration zone at a temperature within the range of from about 38° C. to about 205° C. at a system pressure of from atmospheric to 235 psig an aqueous slurry comprising purified terephthalic acid present as crystals and p-toluic acid present as an aqueous solution and as a co-crystallized form with crystals of said purified terephthalic acid, said filter cell or series of filter cells maintained in suitable position whereby each filter cell develops a filter cake or filter cakes upon introduction of said slurry into each said cell;
   (b) transporting each said filter cell containing said filter cake from said filter zone to a wash zone;
   (c) introducing a water stream into each said filter cell to form a reservoir of water in each filter cell over said filter cake or filter cakes, wherein said water stream is at a pressure gradient of at least 0.5 psi over said system pressure and a temperature in the range of from about 38° C. to about 205° C.;
   (d) washing said filter cake with water for a period sufficient to reduce the concentration of p-toluic acid to equal to or less than 200 ppmw;
   (e) transporting each said filter cell containing washed filter cake to a pressure release zone wherein said system pressure is released to a range from atmospheric to about 90 psig to reduce temperature of said filter cake to a temperature equal to or less than 166° C.; and
   (f) discharging said washed filter cake comprising purified terephthalic acid from each said filter cell wherein the concentration of p-toluic acid in said purified terephthalic acid is equal to or less than 200 ppmw.

2. The process of claim 1 wherein said filter cake is at least 0.5 inches in depth.

3. The process of claim 1 wherein said reservoir of water over said filter cake is at least 0.25 inches in depth.

4. The process of claim 1 wherein said water from washing said filter cake is recovered as wash water and is recycled upstream to slurry crude terephthalic acid or discarded to waste treatment facilities.

5. The process of claim 1 wherein said water stream is at a pressure within the range of from about 0.5 psi to about 65 psi over said system pressure.

6. The process of claim 1 wherein said water stream is at a pressure within the range of from about 5 psi to about 65 psi over said system pressure.

7. The process of claim 1 wherein depth of said filter cake is in the range of from about 0.5 inches to about 8 inches.

8. The process of claim 1 wherein depth of said filter cake is in the range of from about 1 inch to about 4 inches.

9. The process of claim 1 wherein depth of said filter cake is in the range of from about 2 inches to 4 inches.

10. The process of claim 1 wherein said system pressure is in the range of from about 0.5 psig to about 110 psig.

11. The process of claim 1 wherein said system pressure is in the range of from about 40 psig to about 65 psig.

12. The process of claim 1 wherein said temperature of said water stream is in the range of from about 100° C. to about 205° C.

* * * * *

UNITED STATES PATENT OFFICE
CERTIFICATE OF CORRECTION

Patent No. 5,175,355     Dated  December 29, 1992

Inventor(s) Debra J. Streich, Diane J. Graziano, Sandra K. Schiler and Roger J. Grimm It is certified that error appears in the above-identified patent and that said Letters Patent is hereby corrected as shown below:

| Column | Line | |
|---|---|---|
| 4 | 62 | "acid, oxidized" ahould read --acid, is oxidized-- |

Signed and Sealed this

Thirtieth Day of November, 1993

Attest:

BRUCE LEHMAN

Attesting Officer    Commissioner of Patents and Trademarks